(12) United States Patent
Edwards

(10) Patent No.: US 8,282,644 B2
(45) Date of Patent: Oct. 9, 2012

(54) SYSTEM AND METHOD FOR BONE SHORTENING

(76) Inventor: Scott G. Edwards, McLean, VA (US)

( * ) Notice: Subject to any disclaimer, the term of this patent is extended or adjusted under 35 U.S.C. 154(b) by 360 days.

(21) Appl. No.: 12/015,933

(22) Filed: Jan. 17, 2008

(65) Prior Publication Data
US 2008/0172056 A1     Jul. 17, 2008

Related U.S. Application Data

(60) Provisional application No. 60/880,705, filed on Jan. 17, 2007.

(51) Int. Cl.
*A61B 17/58*     (2006.01)
*A61B 17/56*     (2006.01)

(52) U.S. Cl. ......................................................... 606/87

(58) Field of Classification Search .................... 606/86, 606/87, 88, 96, 105, 300, 314, 86 R, 89
See application file for complete search history.

(56) References Cited

U.S. PATENT DOCUMENTS

| | | | |
|---|---|---|---|
| 4,349,018 A | | 9/1982 | Chambers |
| 4,433,681 A | * | 2/1984 | Comparetto ..................... 606/60 |
| 4,565,191 A | * | 1/1986 | Slocum ............................ 606/87 |
| 4,627,425 A | * | 12/1986 | Reese .............................. 606/87 |
| 4,750,481 A | * | 6/1988 | Reese .............................. 606/87 |
| 4,929,247 A | | 5/1990 | Rayhack |
| 4,952,214 A | * | 8/1990 | Comparetto ..................... 606/87 |
| 5,042,983 A | | 8/1991 | Rayhack |
| 5,176,685 A | | 1/1993 | Rayhack |
| 5,254,119 A | * | 10/1993 | Schreiber ........................ 606/87 |
| 5,364,402 A | * | 11/1994 | Mumme et al. ................. 606/88 |
| 5,413,579 A | * | 5/1995 | Tom Du Toit .................. 606/87 |
| 5,449,360 A | * | 9/1995 | Schreiber ........................ 606/87 |
| 5,569,261 A | * | 10/1996 | Marik et al. ..................... 606/88 |
| 5,683,397 A | * | 11/1997 | Vendrely et al. ................ 606/88 |
| 5,779,709 A | | 7/1998 | Harris, Jr. et al. |
| 5,885,296 A | * | 3/1999 | Masini ......................... 606/86 R |
| 5,925,049 A | * | 7/1999 | Gustilo et al. .................. 606/82 |
| 5,935,128 A | * | 8/1999 | Carter et al. ................ 606/86 B |
| 6,007,535 A | | 12/1999 | Rayhack et al. |
| 6,007,537 A | * | 12/1999 | Burkinshaw et al. ........... 606/66 |

(Continued)

FOREIGN PATENT DOCUMENTS
WO     WO 2005/041785 A1     5/2005

OTHER PUBLICATIONS
PCT International Search Report for PCT/US2008/051323; Jun. 2008; 8 pages.

(Continued)

*Primary Examiner* — Kevin T Truong
*Assistant Examiner* — Christopher Beccia
(74) *Attorney, Agent, or Firm* — Alston & Bird LLP

(57) ABSTRACT

An assembly and method for performing a bone shortening osteotomy are provided. An assembly for performing a shortening osteotomy on a bone may include a main guide configured to be coupled to the bone and to guide at least one cut into the bone. The assembly also may include at least a first interchangeable bone resection guide configured to engage the main guide and guide at least one cut into the bone wherein the cuts formed using the main guide and the first interchangeable bone resection guide cooperate to define two bone segments. The two bone segments may then be compressed together and affixed to promote healing of the bone.

34 Claims, 11 Drawing Sheets

U.S. PATENT DOCUMENTS

| | | | |
|---|---|---|---|
| 6,056,754 A * | 5/2000 | Haines et al. | 606/80 |
| 6,187,010 B1 * | 2/2001 | Masini | 606/86 R |
| 6,547,793 B1 * | 4/2003 | McGuire | 606/310 |
| 6,689,139 B2 * | 2/2004 | Horn | 606/87 |
| 6,855,167 B2 | 2/2005 | Shimp et al. | |
| 7,182,766 B1 * | 2/2007 | Mogul | 606/87 |
| 2004/0097946 A1 * | 5/2004 | Dietzel et al. | 606/79 |
| 2004/0138669 A1 | 7/2004 | Horn | |
| 2005/0267484 A1 * | 12/2005 | Menzner | 606/87 |
| 2005/0277941 A1 | 12/2005 | Trumble et al. | |
| 2006/0122617 A1 * | 6/2006 | Lavallee et al. | 606/87 |
| 2007/0276382 A1 * | 11/2007 | Mikhail et al. | 606/62 |
| 2008/0015605 A1 * | 1/2008 | Collazo | 606/87 |

OTHER PUBLICATIONS

ACUMED® Innovative orthopedic implants and accessories; *Ulnar Shortening Plate*; 2 pages; available at <http://www.acumed.net> (visited Nov. 29, 2007).

Rayhack® Osteotomy Systems Creative Medical Designs, Inc.; *Ulnar Shortening Osteotomy—Generation II*; 3 pages; available at <http://www.rayhack.com/ulnar.htm> (visited Jan. 18, 2008).

Rayhack® Osteotomy Systems; Precision Oblique Ulnar Shortening—Surgical Technique Manual; Revised May 1, 2005; 17 pages; Copyright © 2005 Creative Medical Designs™, Inc.

* cited by examiner

SYSTEM AND METHOD FOR BONE SHORTENING

CROSS-REFERENCE TO RELATED APPLICATIONS

This application claims the benefit of U.S. Provisional Application No. 60/880,705, filed Jan. 17, 2007, which is hereby incorporated in its entirety by reference.

FIELD OF THE INVENTION

Embodiments of the present invention relate to devices for surgically shortening a bone and, more specifically, for performing a shortening osteotomy on a bone by cutting away part of the bone, drawing the remaining segments together, and securing the segments to heal.

BACKGROUND OF THE INVENTION

Ulnar impaction syndrome is a condition in which the ulna bone is too long in relation to the radius bone resulting in impaction of the carpal bones in the wrist. The impacted carpal bones and impinged soft tissues can cause pain and swelling while limiting the range of motion in the wrist. The long term effects of ulnar impaction syndrome can include ligament attenuation and tearing resulting in chronic pain, carpal instability, and permanent arthritis due to the deterioration of the cartilage between the ulna and the carpal bones. To mitigate the symptoms and preclude long-term effects, the ulna can be shortened to a length that corresponds to the length of the radius, thereby reducing or eliminating the impaction on the carpal bones.

Surgically shortening the ulna is typically performed by two cuts made perpendicular to the axis of the ulna to remove the length of bone that the ulna is desired to be shortened by. The two bone segments that remain are then compressed and joined by plates and screws. This method reveals several disadvantages. The first disadvantage is that the relatively small surface area over which the union must occur, which magnifies the effect of any discontinuity or anomaly in the union. These anomalies may result in incomplete healing or nonunion that is susceptible to breakage. Another disadvantage of using this technique is that there is very little room for error when removing the section of bone and removing too much could result in an ulna that is too short. A third disadvantage resulting from using this technique is the plate that is required to hold the bone sections together may be uncomfortable for the patient and may require removal of the plate after the bone has healed, which may be costly, inconvenient, and subjects the patient to the risks of another surgery and anesthesia.

Another method for shortening the ulna involves a diagonal or oblique cut across the ulna. This method is outlined in U.S. Pat. No. 6,689,139 and while it may mitigate the disadvantages of the previously mentioned method, the diagonal cut may introduce other disadvantages when shortening the ulna. The '139 patent discloses a guide that mounts to the ulna and provides a diagonal surface along which a surgeon may sever the ulna. The ulna is then shortened by sliding the opposing sides of the angled cut relative to each other. Since the oblique cuts tend to overlap in compression, there is a risk of bony prominence. The bony prominence may be a source of discomfort for the patient and require further surgery. Another disadvantage that may result from using a diagonal cut to shorten the ulna is that over compression may cause the ulna to be inappropriately shortened too much. A third disadvantage of using the device of the '139 patent is that, during surgery, the bone typically must be held securely in place by the surgeon or some other mechanism while screws are inserted across the diagonal cut.

Therefore, a need exists for a device to aid in performing a shortening osteotomy that overcomes the disadvantages of the aforementioned techniques and is relatively simple to use. In addition, there is a need for a device that facilitates bone healing following a shortening osteotomy.

SUMMARY OF THE INVENTION

Embodiments of the present invention may provide improvements over the prior art by, among other things, providing systems and methods for performing a shortening osteotomy on a bone. For example, a system for performing a shortening osteotomy on a bone may include a main guide configured to be coupled to the bone and to guide at least one cut into the bone. The assembly also includes at least a first interchangeable bone resection guide configured to engage the main guide and guide at least one cut into the bone wherein the cuts formed using the main guide and the first interchangeable bone resection guide cooperate to define two bone segments.

According to aspects of the system, the main guide includes a plurality of holes and slots each configured to guide a respective temporary fastener (e.g., a K-wire or pin) into the bone. The slots may extend transversely, longitudinally, or obliquely through the main guide and may be configured to guide respective temporary fasteners into the bone so as to facilitate compression between the two bone segments. In addition, the system may further include a clamp configured to engage the plurality of temporary fasteners positioned within the plurality of slots and to bias the plurality of temporary fasteners so as to compress the two bone segments together.

Additional aspects of the system include a main guide having a slot configured to guide a plurality of cuts within the bone, wherein the slot comprises first and second transverse portions and a longitudinal portion extending therebetween. The first interchangeable bone resection guide may be configured to overlie a portion of the main guide and may include a pair of surfaces configured to align with the first and second transverse portions to define a pair of cutting guides. The first interchangeable bone resection guide may include at least one alignment hole, and the main guide may include at least one alignment pin configured to engage the at least one alignment hole. Furthermore, the system may include at least a second interchangeable bone resection guide configured to engage and be disengaged from the main guide and to guide at least one cut into the bone having a different location or direction than the at least one cut formed using the first interchangeable bone resection guide. The main guide may include first and second portions arranged in an L-shape or C-shape, and the first portion of the main guide may be configured to guide at least one cut into the bone, while the second portion of the main guide may include at least one hole configured to receive and guide a respective screw or other fastener into the bone so as to secure the two bone segments together.

An additional embodiment of the present invention provides a system for performing a shortening osteotomy on a bone. The system includes a main guide including a plurality of openings and configured to be coupled to a bone and to guide at least one cut into the bone, and a bone resection guide configured to be coupled to the main guide and to guide at least one cut into the bone. The cuts formed using the main guide and the bone resection guide cooperate to define two bone segments, wherein the plurality of openings are configured to guide respective temporary fasteners into the bone and facilitate compression between the two bone segments. The openings may extend obliquely through the main guide and may be slotted.

According to another embodiment of the present invention, a method for performing a shortening osteotomy on a bone is provided. The method includes attaching a main guide to a bone, coupling a first bone resection guide to the main guide, and forming at least one cut using the first bone resection guide. The method further includes forming at least one cut using the main guide such that the cuts formed using the main guide and the first bone resection guide define two bone segments, compressing the two bone segments together, and securing the two bone segments together.

Variations of the method include attaching the main guide to the bone using a plurality of temporary fasteners guided into the bone with a plurality of respective holes defined in the main guide. The coupling step may include mating at least one alignment hole defined in the first bone resection guide into engagement with at least one respective alignment pin extending from the main guide. Alternatively, the coupling step may include mating at least one alignment hole defined in the main guide into engagement with at least one respective alignment pin extending from the bone resection guide. The compressing step may include urging together a plurality of temporary fasteners guided into the two bone segments along a plurality of respective slots defined in the main guide. The securing step may include securing the two bone segments together with at least one fastener extending through the two bone segments.

In addition, the step of forming the at least one cut using the first bone resection guide may include forming a pair of transverse cuts, while the step of forming the at least one cut using the main guide may include forming a longitudinal cut extending between the pair of transverse cuts. Forming the pair of transverse cuts may include forming the transverse cuts perpendicular to a longitudinal axis of the bone, while forming the longitudinal cut may include forming the longitudinal cut parallel to a longitudinal axis of the bone. Moreover, the method may also include detaching the first bone resection guide from the main guide, coupling a second bone resection guide to the main guide, if necessary, and forming at least one cut using the second bone resection guide that is different than the at least one cut formed using the first bone resection guide. Another embodiment may utilize the main guide as the first cutting guide, and a single bone resection guide as the second cutting guide. The securing step may include securing the two bone segments together while the two bone segments are being compressed. The attaching step may include orienting the main guide such that a first portion of the main guide contacts an exposed side of the bone, and a second portion of the main guide contacts a perpendicular side of the bone, perhaps anterior, posterior, medial or lateral.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE DRAWINGS

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention generally relate to a system for performing a shortening osteotomy of a bone. According to one embodiment, the system generally includes a main guide 10 and one or more bone resection guides 50, 70 that are employed to form a plurality of cuts in a bone. The cuts define two bone segments that may be brought together under compression and secured in position, as explained in further detail below. The system may be used to perform, for example, an ulnar or radial shortening osteotomy, a femoral or humoral shortening osteotomy, or a tibial or fibular shortening osteotomy, metacarpal, metatarsal or phalangeal shortening osteotomies, among other bone shortening osteotomies. For ease of explanation, however, the specification and accompanying figures will refer to an ulnar shortening osteotomy, although it is to be understood that other shortening osteotomies may be accomplished using other embodiments of the device described herein.

Figure 1A:
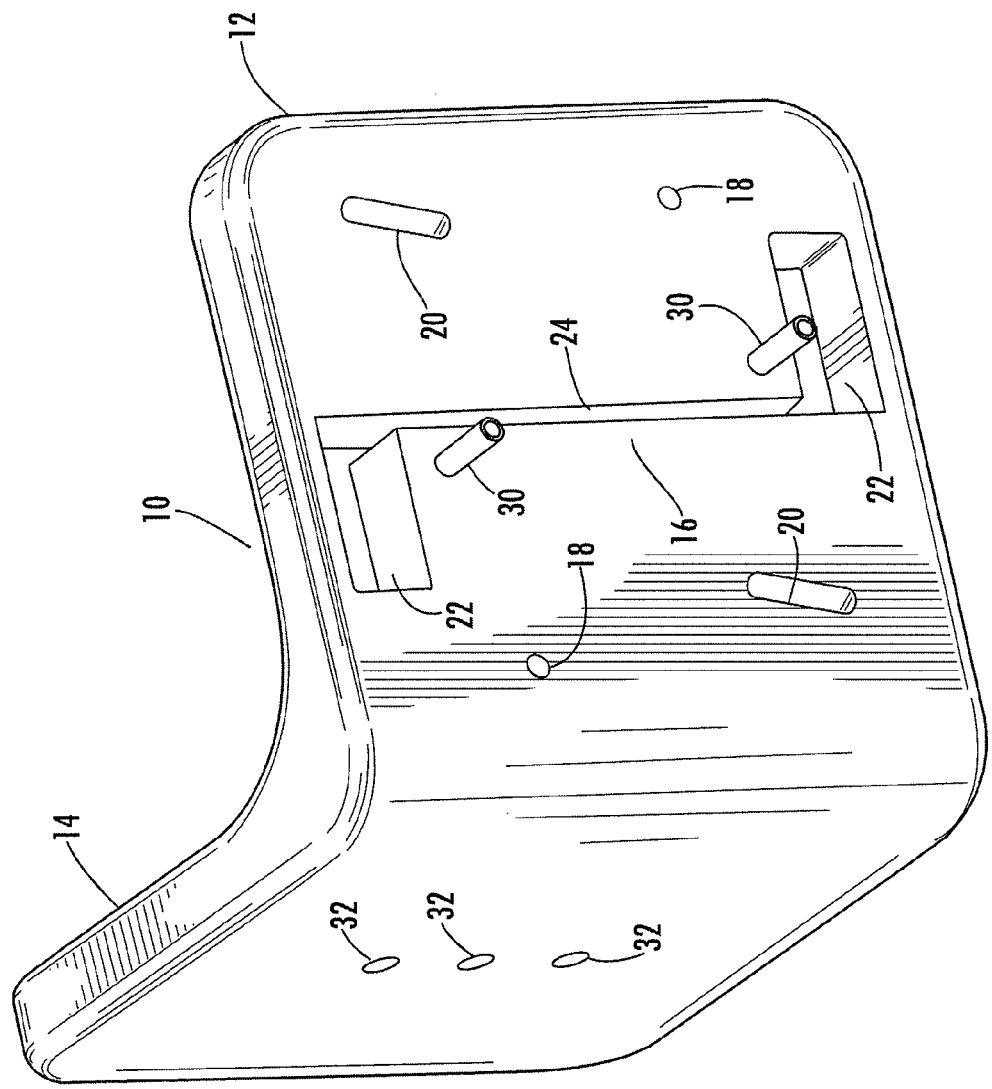
FIG. 1A is a perspective view of a main guide according to one embodiment of the present invention.
Figure 1B:
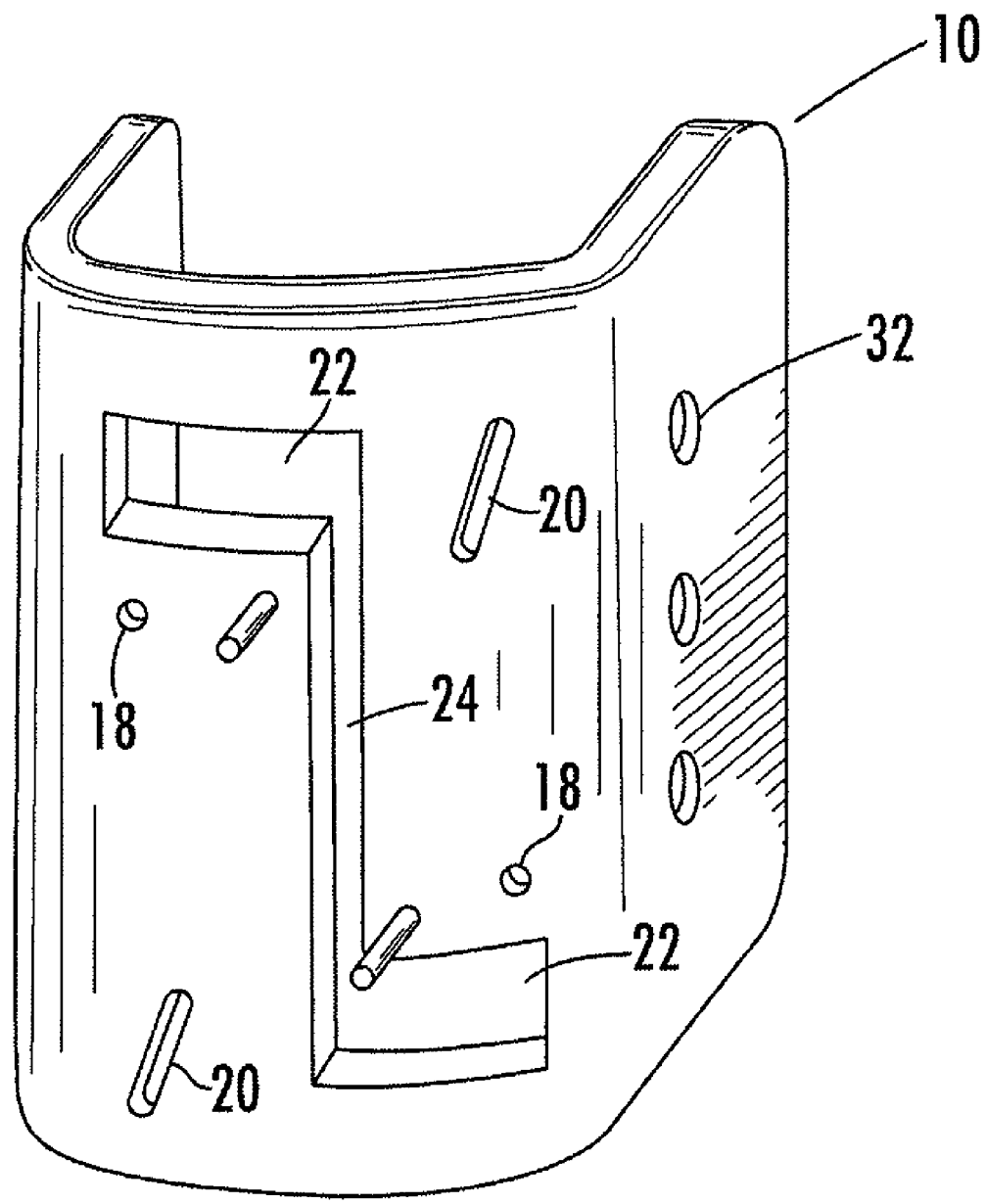
FIG. 1B is a perspective view of a main guide according to a second embodiment of the present invention.

Referring to FIG. 1A, a main guide 10 for an ulnar shortening osteotomy system according to one embodiment is shown. The main guide 10 is generally L-shaped and includes a first plate 12 and a second plate 14. Alternatively, the main guide 10 may be C-shaped to conform to the cylinder surface of the cortical bone as shown in FIG. 1B. The main second plate 14 is disposed adjacent to the first plate 12, which may be attached along a longitudinal edge generally forming a right angle. However, the plates 12, 14 could be integrally defined. Both plates 12, 14 of the main guide 10 are made from a material suitable for sterile surgical use that is hard enough to serve as a cutting guide for a bone or sagittal saw, such as stainless steel, titanium, cobalt chrome, carbon fiber, or plastic. The first plate 12 of the main guide 10 may be configured to contact the exposed side of the bone while the second plate 14 of the main guide 10 may be configured to contact either the anterior 42 or posterior 44 side of the bone depending on the surgeon's preference. The size and configuration of the main guide 10 may vary depending on the size of bone that the main guide 10 is to be positioned on. For example, a main guide 10 for an adult femur will be larger than a main guide 10 for a child's ulna. The shape may also vary due to the variable surfaces of the bone and the amount of openings or fasteners required for an indicated purpose.

FIG. 1A illustrates a slot 16 that passes entirely through the first plate of the main guide 10. The slot 16 may have two transverse portions 22 interconnected by a longitudinal portion 24. The transverse portions 22 of the slot 16 may be at least as wide as half of the bone to be operated on while the height of each transverse slot may be as great as the largest shortening osteotomy to be performed. The longitudinal slot 24 is situated between the transverse slots 22 and is wide enough for a bone or sagittal saw to pass through. The length of the longitudinal 24 slot and width of the transverse slots 22 can vary depending on the size of bone that the main guide 10 is designed for. For example, a main guide 10 for an adult femur will be larger than a main guide 10 for a child's ulna. The shape may also vary due to the variable surfaces of the bone and the amount of openings or fasteners required for an indicated purpose. One of the transverse slots 22 may extend from the longitudinal slot 24 to the anterior side of the bone 42, while the other transverse slot 22 may extend from the opposite end of the longitudinal slot 24 to the posterior side of the bone 44, as shown in FIG. 2.

The main guide 10 may have at least two holes 18 that extend through the first plate 12 located proximate to the ends of the transverse slots 22 and on opposite sides of the longitudinal slot 24. The holes 18 may be located cattycorner or diagonally from one another on the first plate 12. These holes 18 may be sized and configured to receive temporary fasteners 36, such as pins, bolts, screws, tenaculums, clamps, or Kirschner Wires, also known as K-wires, in order to secure the main guide 10 to the bone, as shown in FIG. 2. The fasteners 36 positioned through the holes 18 and into the bone may prevent rotation or translation of the main guide 10 when attached to the bone. The holes 18 may be angled through the main guide 10 to aid insertion of the fasteners 36 into the bone, as well as to resist the tendency of the main guide to travel away from the bone along the axis of the fasteners. The holes 18 may be oriented obliquely toward the center of the main guide 10, as shown in FIG. 2.

Angled slots 20 may also be defined in the first plate 12 and located in the corners of the first plate 12 opposite the holes 18. Thus, the angled slots 20 extend transversely, obliquely, convergently, divergently, or parallel through the first plate 12 and may be located catacorner or diagonally from one another on the first plate. These angled slots 20 may be configured to receive fasteners 38 guide the fasteners into the bone, which may later be used for compression of the two bone segments together. The angled slots 20 are generally longitudinal, and are angled towards the center of the first plate 12 in order to facilitate compression of the bone segments together as explained in further detail below.

Figure 2:
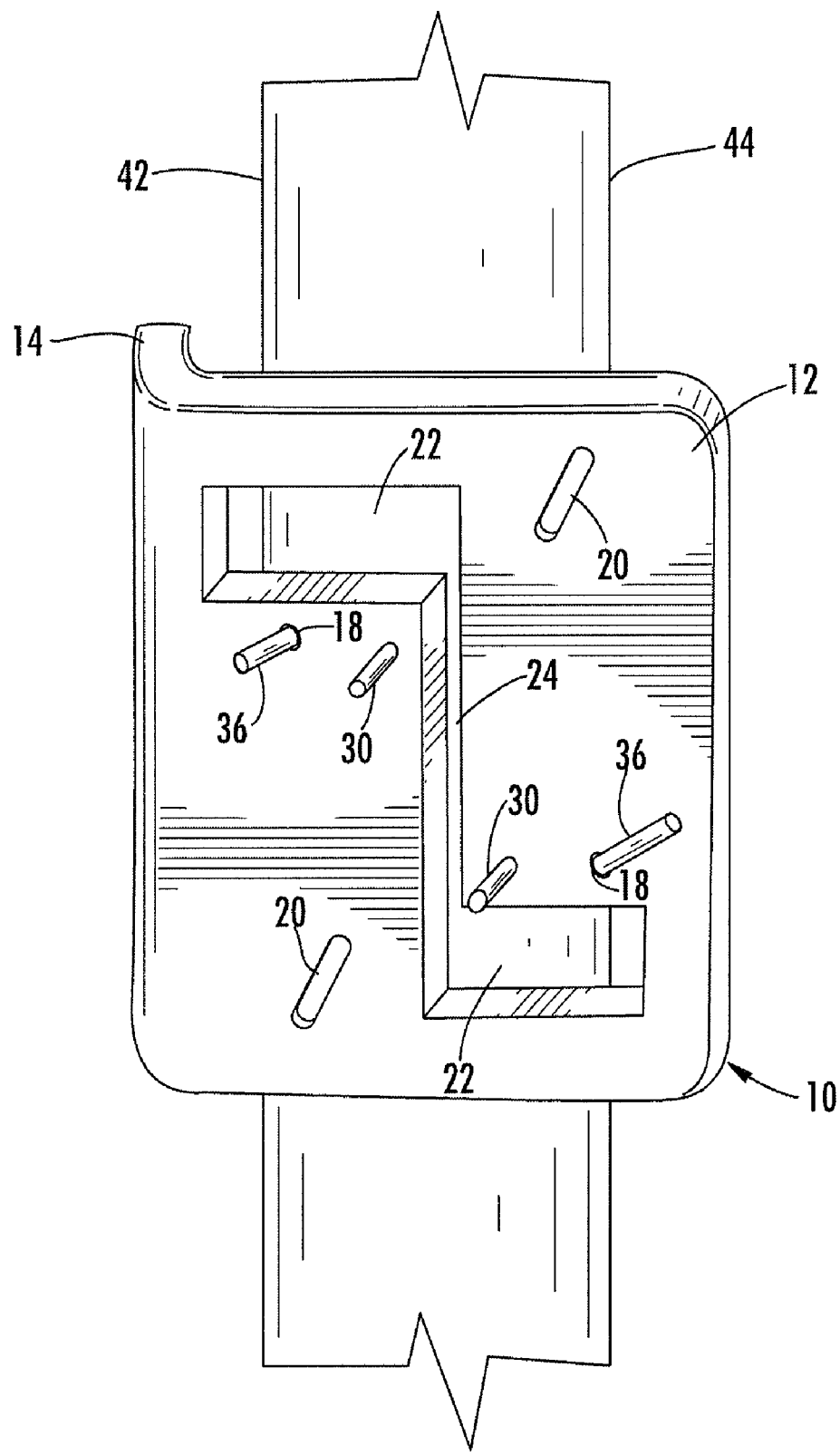
FIG. 2 shows a perspective view of a main guide attached to a bone on which a shortening osteotomy is to be performed according to an embodiment of the present invention.

It is appreciated that while the embodiments shown in FIGS. 1 and 2 illustrate the use of K-wires 36 to temporarily secure the main guide 10 to the bone, other embodiments may include a variety of other techniques for securing the main guide to the bone such as screws, adhesives, pins, or bands among others.

Alignment pins 30 may extend from the first plate 12 of the main guide 10 proximate to the internal corners created by the longitudinal slot 24 and each of the transverse slots 22. These alignment pins 30 extend away from the top surface of the first plate 12 and opposite the bottom surface of the first plate that is in contact with the bone. As explained in further detail below, the alignment pins 30 may be sized and configured to engage a respective bone resection plate 50, 70.

The second plate 14 may have through holes 32 defined therethrough and configured to receive fasteners. The holes 32 may be aligned in parallel with respect to one another, as shown in FIG. 1A. It is appreciated that although the pictured embodiment discloses three through holes 32, the number and location of the holes may be varied for different applications and in applications with larger bones, the holes 32 need not necessarily be in parallel, of equal diameter, or equidistant from one another.

According to one embodiment and referring to FIG. 2, the main guide 10 is shown in position over the bone on which the shortening osteotomy is to be performed. The main guide 10 may be attached to the bone using the fasteners 36 secured in the holes 18 in the first plate 12. Fasteners 38 may also be attached to the bone through the angled slots 20 in the first plate 12. The transverse slots 22 are configured to extend from the longitudinal slot 24 to at least the anterior 42 and posterior 44 edge of the bone. The first plate 12 of the main guide 10 may be configured to be in contact with the exposed side of the bone while the second plate 14 of the main guide 10 may be configured to be in contact with either the anterior 42 or posterior 44 side of the bone depending on the surgeon's preference.

Figure 3A:
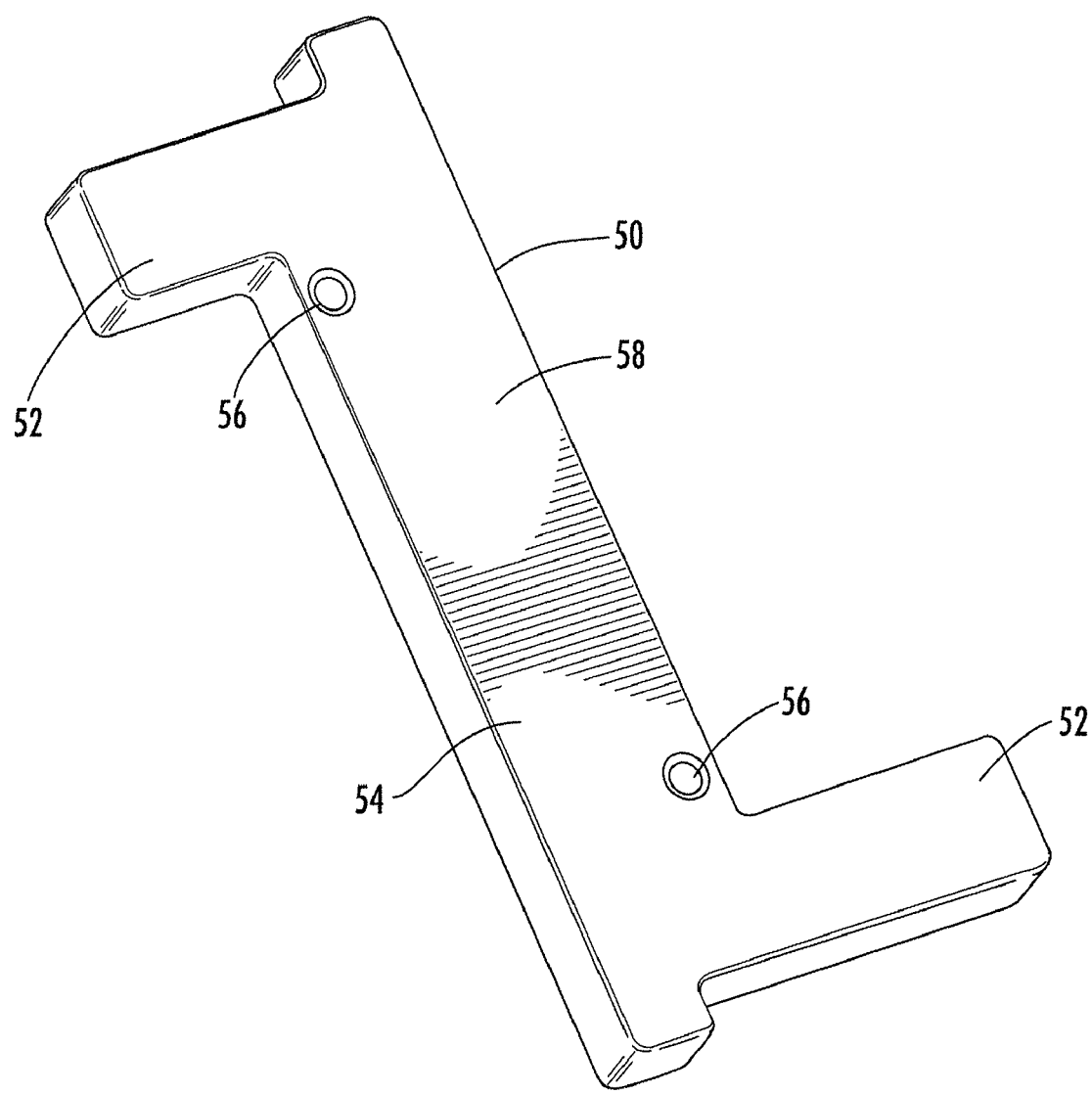
FIG. 3A is a perspective view of a bone resection guide according to one embodiment of the present invention.

Referring to FIG. 3A, a first bone resection guide 50 is shown according to one embodiment. The system may employ one or more bone resection guides that cooperate with the main guide in order to guide a saw into the bone to form cuts therein. Thus, the bone resection guides may be interchangeable and used to form sequential cuts having predetermined sizes. The choice of bone resection guides used may depend on the amount of bone shortening desired. Each bone resection guide 50 will be sized according to the amount of bone shortening desired. The first bone resection guide 50 may be comprised of two transverse portions 52 joined by a longitudinal portion 54. The first bone resection guide 50 may be made from a hard material suitable for use in a sterile surgical environment, such as stainless steel suitable for use as a cutting guide for a saw blade. Two alignment holes 56 may be sized and configured to receive and engage the alignment pins 30 of the main guide 10. The bone resection guide 50 may be marked with a measurement 58 or reference number to indicate the size of shortening osteotomy it is intended for.

Figure 4:
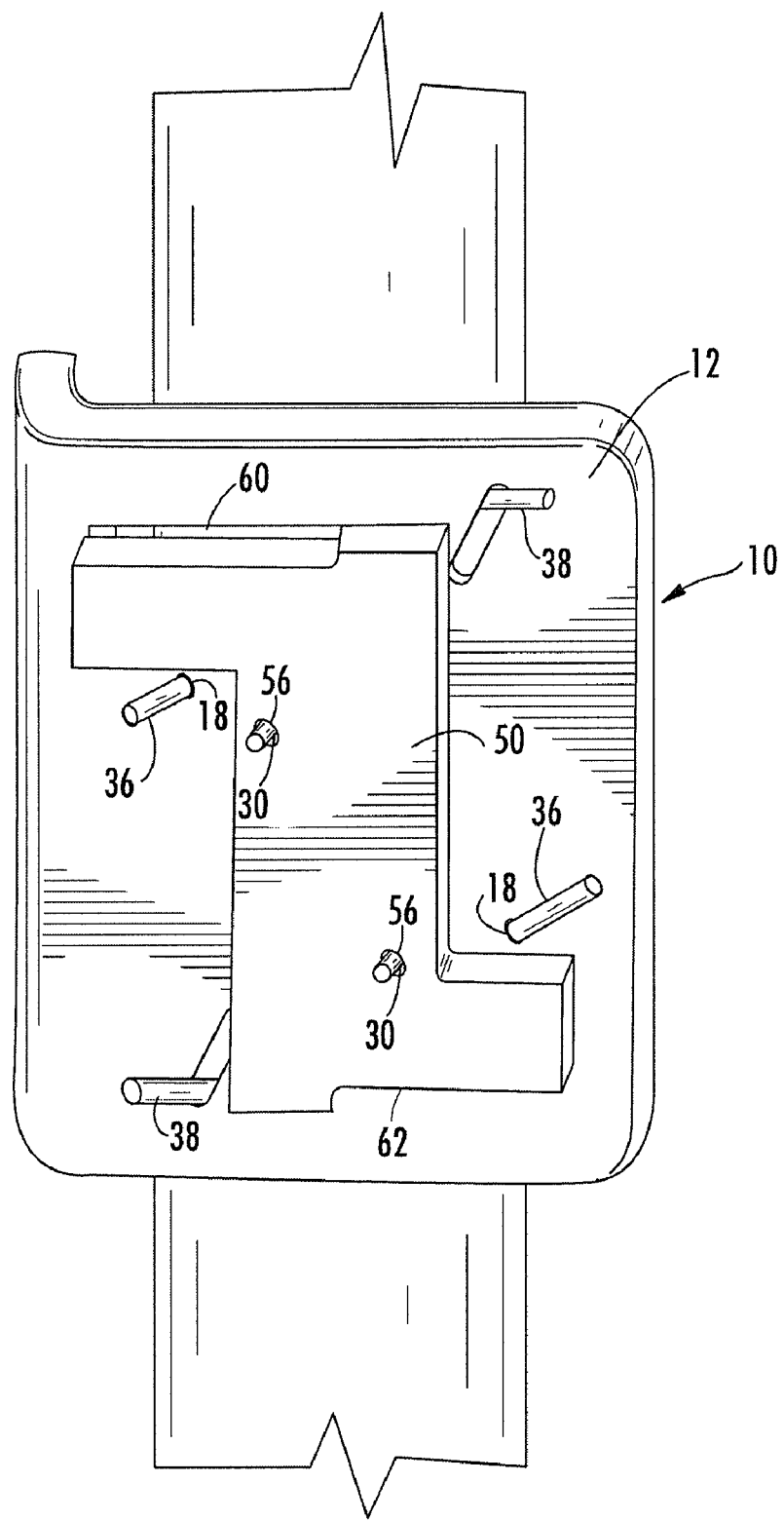
FIG. 4 is a perspective view of the bone resection guide of FIG. 3A aligned on the main guide shown in FIG. 2 according to an embodiment of the present invention.
Figure 7:
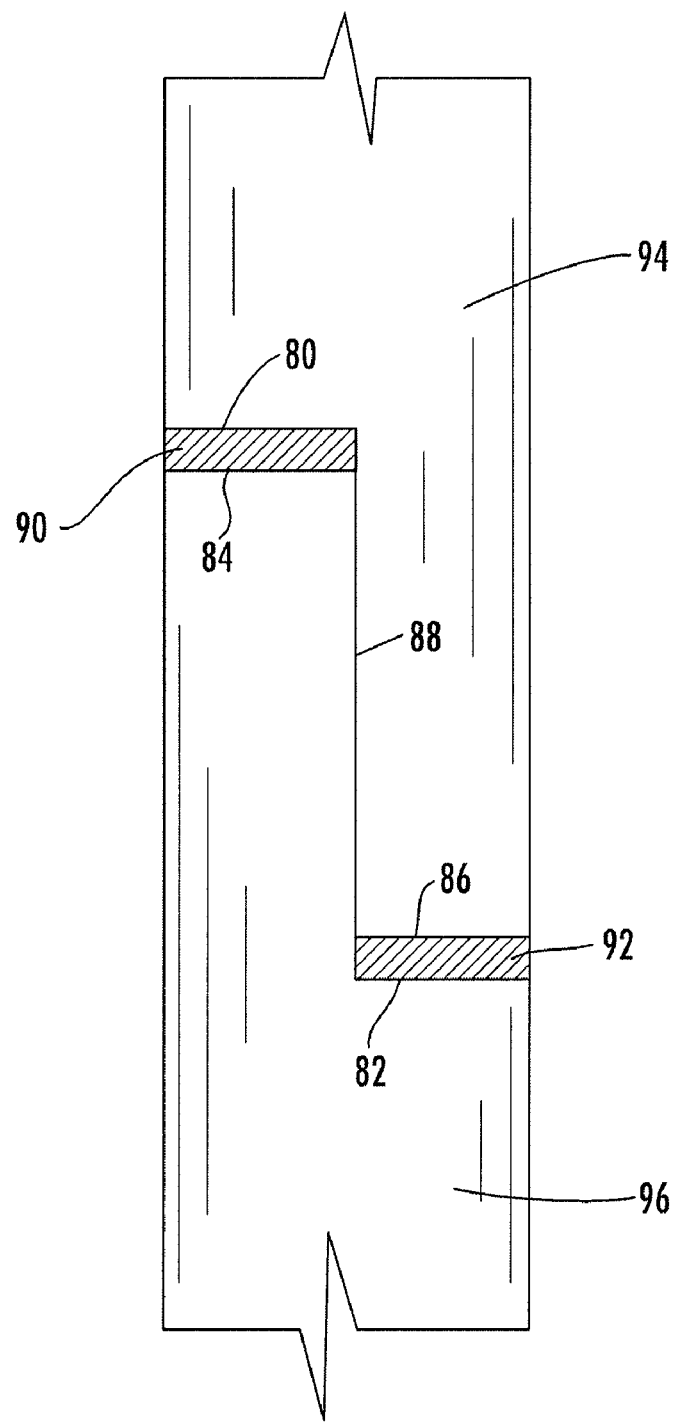
FIG. 7 shows a plan view of bone material to be removed during a shortening osteotomy according to one embodiment of the present invention.

FIG. 4 shows the first bone resection guide 50 aligned on top of the first plate 12 of the main guide 10 according to one embodiment of the present invention. The alignment pins 30 of the main guide are inserted through the alignment holes 56 of the first bone resection guide 50 in order to secure the first resection guide to the main guide 10. The first bone resection guide 50 is configured to overlie the longitudinal slot 24 of the main guide 10 and partially overlie each of the two transverse slots 22. The exposed portion of the transverse slots 22 in the main guide 10 defines first and second transverse cutting guides 60, 62. Each of the first and second transverse cutting guides 60, 62 extend the entire width of the respective transverse slot 22. The width and height of the first and second transverse cutting guides 60, 62 are sized and configured to receive a bone or sagittal saw blade. A saw may be inserted through the first and second transverse cutting guides 60, 62 to saw through the bone creating first and second transverse cuts 80, 82 as shown in FIG. 7, wherein the cuts correspond to the width and height of the first and second transverse cutting guides.

Figure 5:
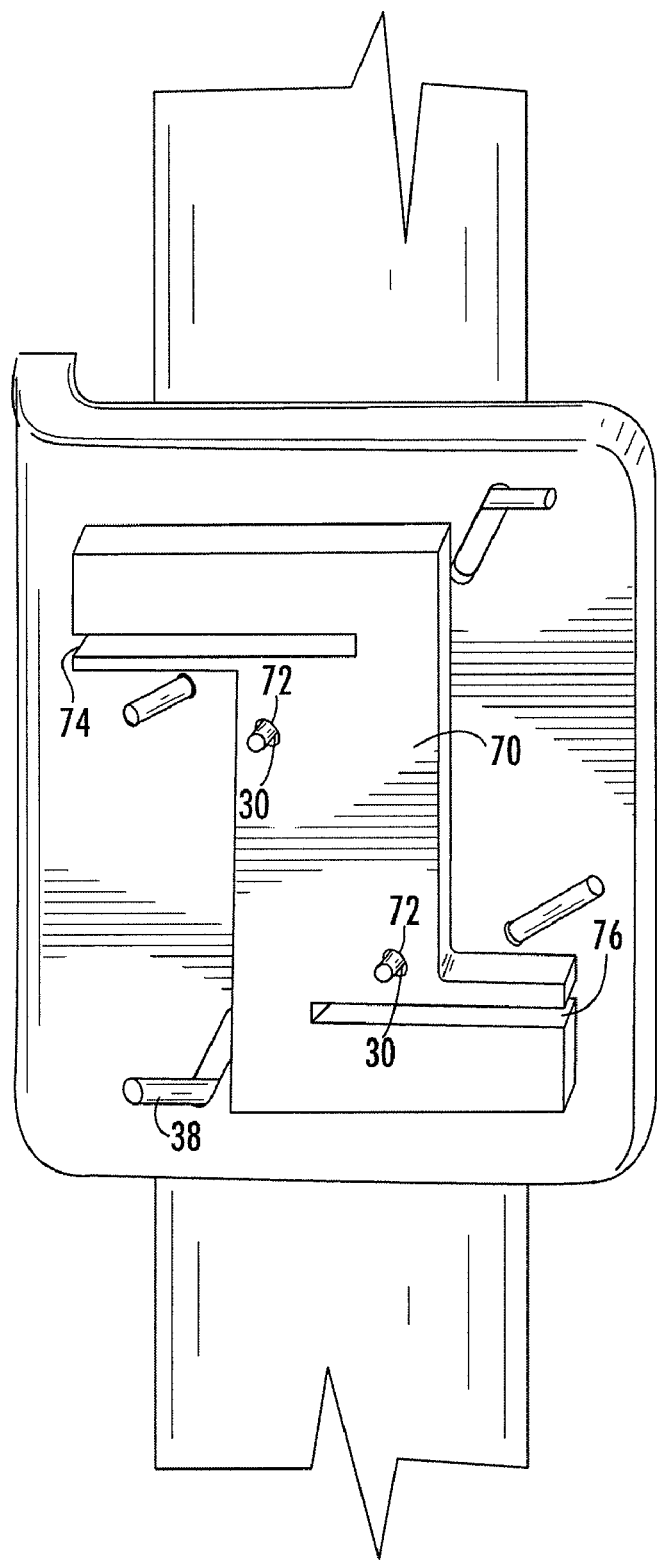
FIG. 5 shows a second bone resection guide aligned on the main guide of FIG. 2 according to an additional embodiment of the present invention.

FIG. 5 shows a second bone resection guide 70 which may be coupled to the main guide 10 after removing the first bone resection guide 50. Thus, as before, the second bone resection guide 70 may be secure to the main guide 10 by aligning the alignment pins of the main guide 10 with the alignment holes 72 of the second bone resection guide 70. The second bone resection guide 70 is similar to the first bone resection guide 50 in that it is configured to overlie the longitudinal slot 24 in the main guide 10. The second bone resection guide 70 includes slots that define third and fourth transverse cutting guides 74, 76 and is configured to partially overlie the transverse slots 22 in the main guide 22 when the second bone resection guide 70 is aligned on the main guide 10. The third and fourth transverse cutting guides 74, 76 are spaced a predetermined distance from where the first and second transverse cutting guides 60, 62 were located. The third and fourth cutting guides 74, 76 may be at least as wide as half of the bone width and of sufficient height to receive a bone or sagittal saw blade. The distance between the first and third cutting guides 60, 74 and the second and fourth cutting guides 62, 76 is dictated by the second bone resection guide 70. The appropriate second bone resection guide 70 may be selected by the surgeon based on the distance by which the bone needs to be shortened. For example, the distance may be determined prior to surgery based on X-ray measurements.

While the second bone resection guide 70 shown in the pictured embodiment encloses the third and fourth cutting guides 74, 76, it is appreciated that other embodiments of the second bone resection guide 70 may use the transverse slots 22 of the main guide as part of the third and fourth cutting guides 74, 76.

Figure 6A:
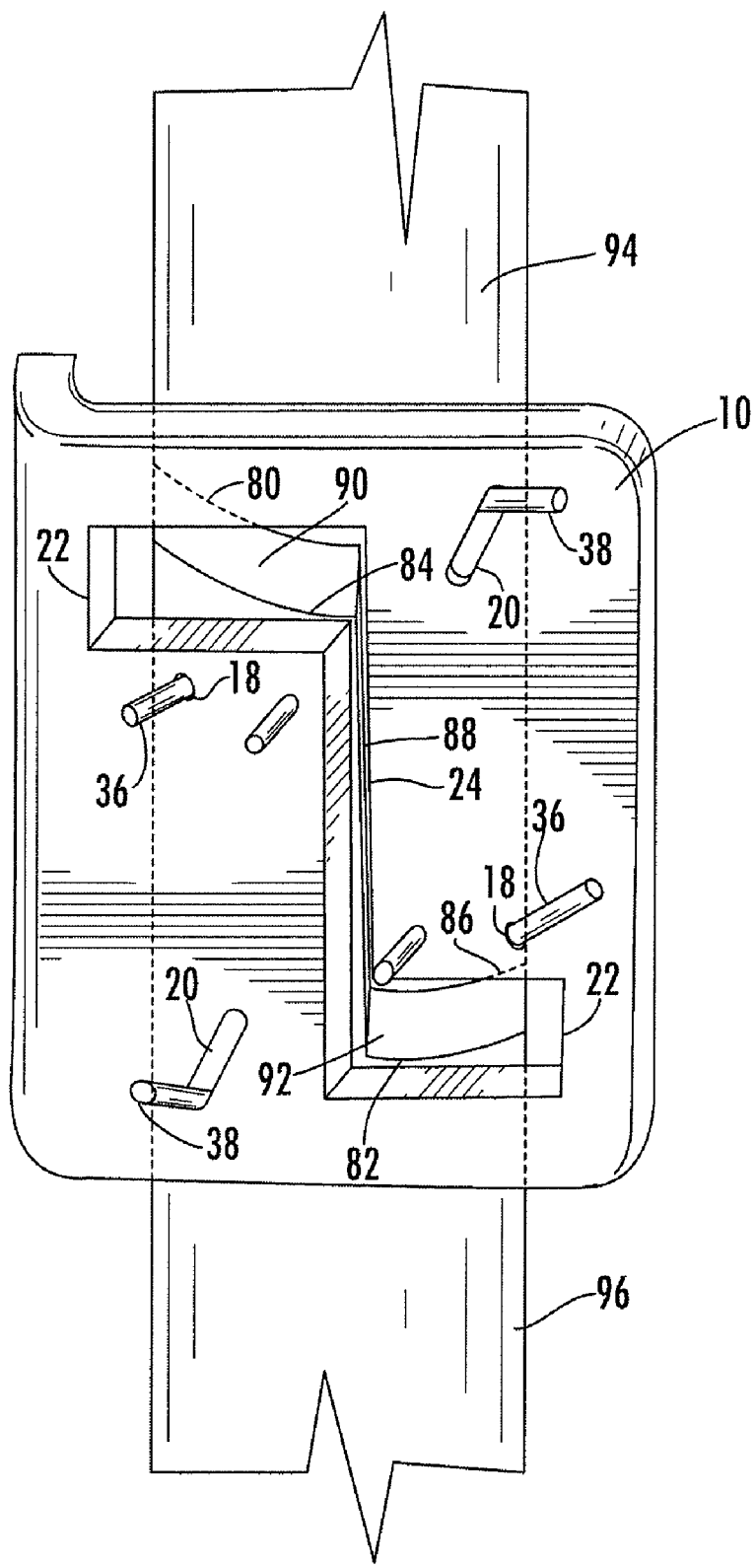
FIG. 6A shows the main guide of FIG. 2 after the second bone resection guide has been removed.

Referring to FIG. 6A, the main guide 10 is shown with the second bone resection guide 70 removed to reveal the transverse slots 22 and the longitudinal slot 24. The bone may then be cut through the longitudinal slot 24. This cut 88 severs the bone between the first and second transverse cuts 80, 82 that were previously made in order to define two bone segments 94, 96. The resulting bone fragments 90, 92 may then be removed.

The fasteners 36 that are attached to the bone through the holes 18 in the main guide 10 may be removed from the bone and from the main guide such that movement between the bone segments 94, 96 is possible. The fasteners 38 that are attached to the bone through the angled slots 20 in the main guide allow the compression to not only be applied longitudinally, but also transversely, thus applying pressure across all three surfaces that were created 80, 82, 88. Further, as compression force is applied to the bone segments 94,96, the fasteners 38 in angled slots 20 in the main guide prevent unwanted rotation, translation, and malalignment.

Figure 6B:
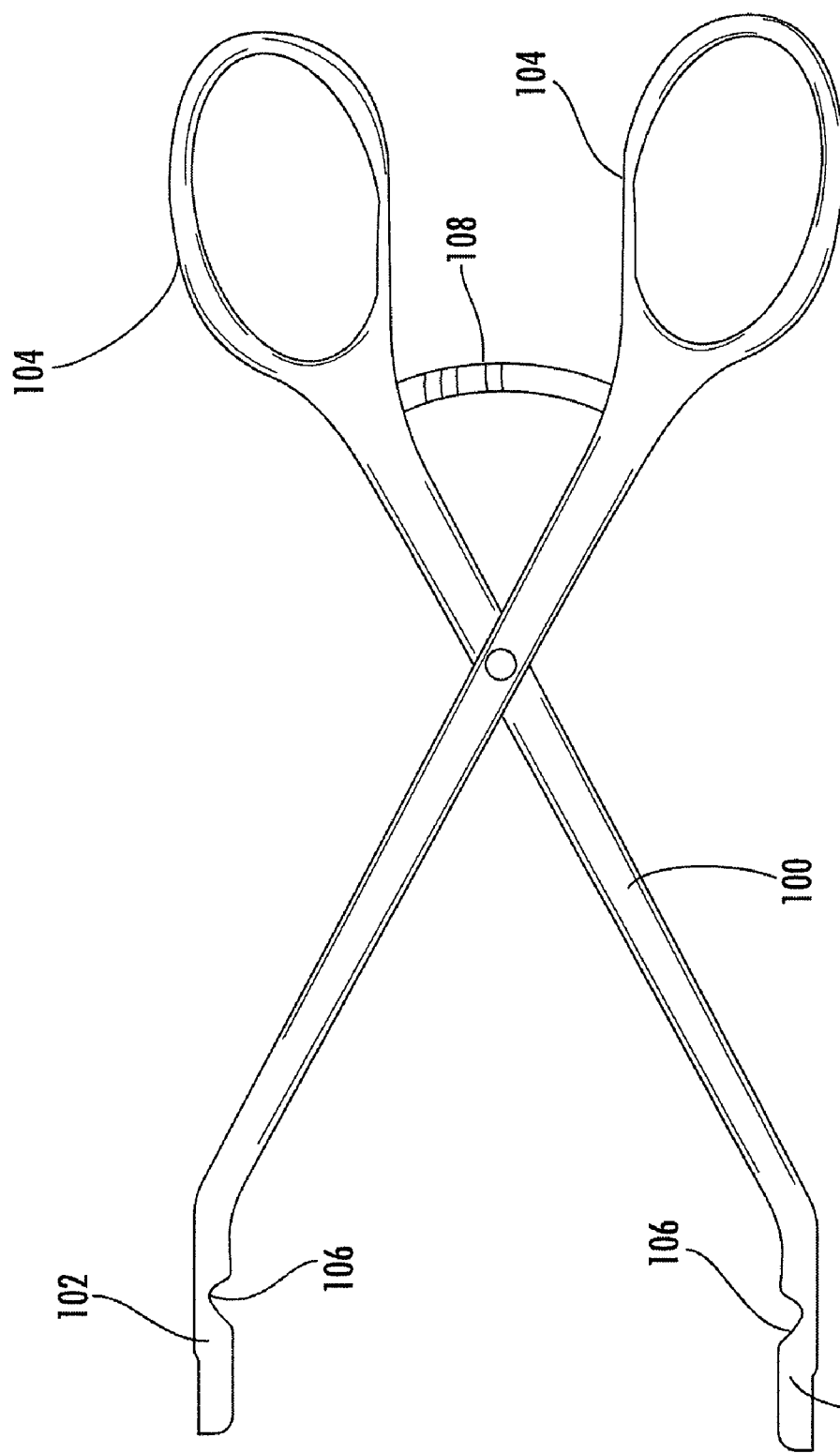
FIG. 6B shows a compression clamp used to compress the bone segments together according to one embodiment of the present invention.

According to one embodiment, a compression clamp 100 (as shown in FIG. 6B) is employed to compress the two bone segments together. The ends 102 of the compression clamp 100 include slots 106 that are configured to engage the ends of the fasteners 38 extending from the main guide 10, while a surgeon may manipulate the clamp via finger grips 104. In addition, the compression clamp 100 may include a locking mechanism 108 that allows the surgeon to lock the clamp when a desired compression is achieved so that the surgeon may perform additional procedures, such as inserting the screws 98 within the bone while the bone segments 94, 96 are being compressed.

Figure 3B:
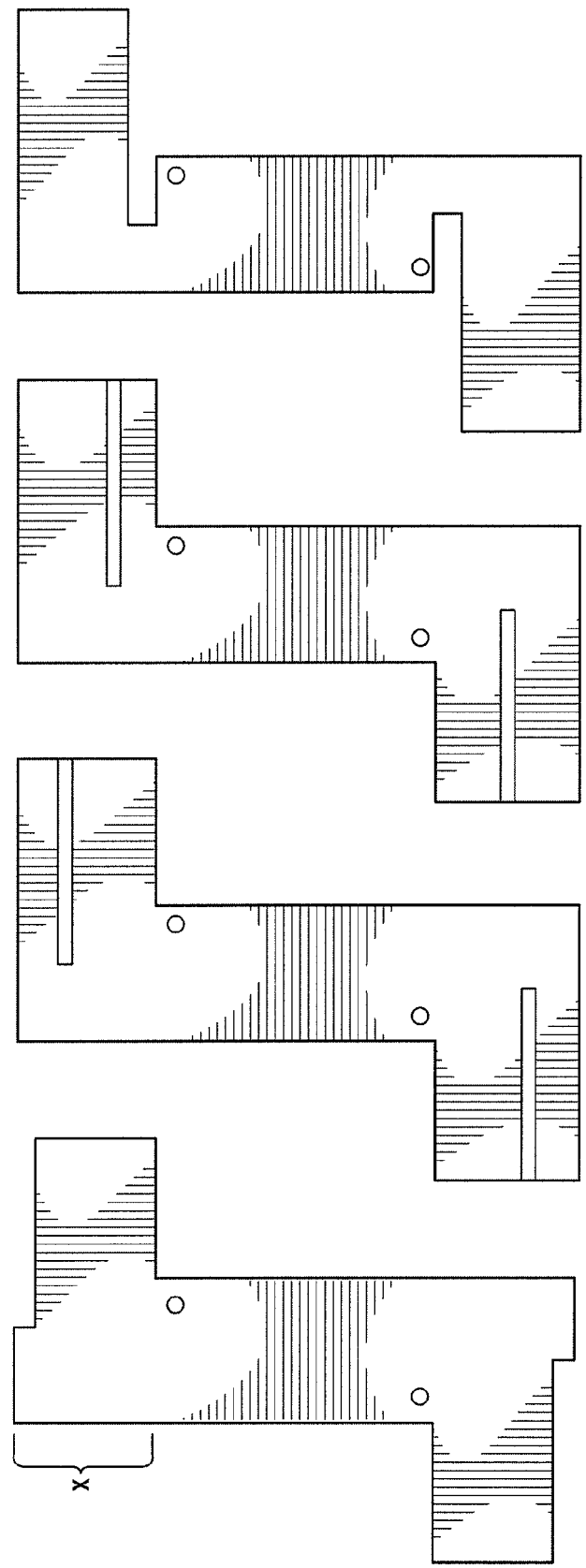
FIG. 3B shows a plan view of various configurations of bone resection guides according to additional embodiments of the present invention.

FIG. 7 illustrates the cuts that may be made in a shortening osteotomy process according to one embodiment. First and second cuts 80, 82 may be made first using a first bone resection guide 50, followed by the third and fourth cuts 84, 86 that are made using a second bone resection guide 70. Typical length of bone that is removed may vary, for example, between 2 to 20 mm. The final cut 88 may be made longitudinally between the first and second cuts 80, 82 via a main guide 10, which creates two separate bone segments 94, 96, together with two bone fragments 90, 92 which may be removed. As described above, the number of bone resection guides employed may depend on a variety of factors, such as the patient or surgeon preference. For example, FIG. 3B shows four bone resection guides that may be used in succession to incrementally remove bone (e.g., 2 mm, 3 mm, 4 mm, and 5 mm bone resection guides). Alternatively, bone may be resected in one block with one guide rather than incrementally with several guides. In addition, although FIGS. 4 and 5 illustrate the use of more than one bone resection guide, another embodiment may utilize the main guide as one of the cutting guides, and a single bone resection guide as the second cutting guide. Further, although the term "transverse" has been used to describe the transverse slots 22, this should not be limited to mean that the slots and the resultant cuts are straight and/or angled at exactly 90° relative to the long axis of the bone or the longitudinal slot 24.

Figure 8:
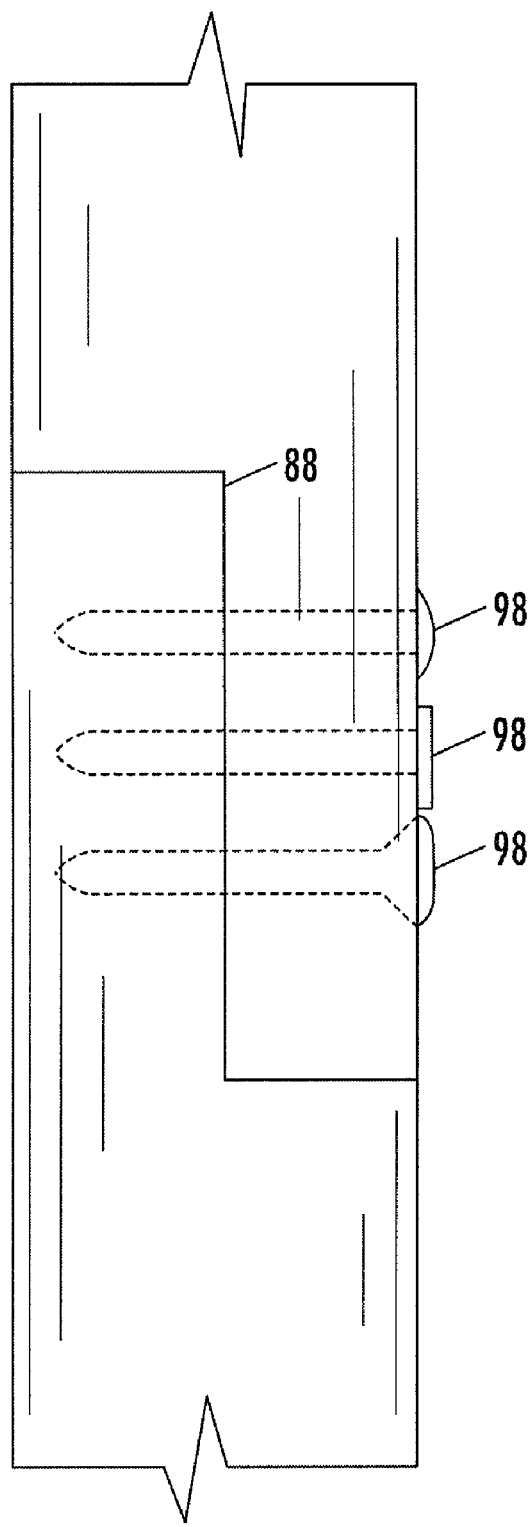
FIG. 8 shows a plan view of a plurality of screws inserted across a longitudinal cut between bone sections cut during a shortening osteotomy according to an embodiment of the present invention.

As shown in FIG. 8, three holes may be drilled across the longitudinal cut line 88 by guiding a drill through the holes 32 in the second plate 14 of the main guide 10. Screws 98 may then be inserted into respective holes to secure the two bone segments 94, 96 together. The first screw 98 is intended to generate compression at the osteotomy site and may be inserted in the center hole using a partially-threaded screw or a fully-threaded screw using lag-technique, then the remaining screw or screws may be inserted using standard technique with a fully-threaded screw. The screws may either be countersunk into the bone or they may be low-profile to ensure minimal irritation to the patient. The fasteners 38 used to compress the bone segments 94, 96 together may be removed from the bone and the main guide 10 removed from the bone. It is appreciated that while screws are illustrated in the embodiment shown, a variety of other fasteners are suitable for the application such as pins or wires. Over time, the bone segments 94, 96 will fuse together.

The first and second transverse cutting guides 60, 62 (as shown in FIG. 4) may be color coded a first color. The third and fourth transverse cutting guides 74, 76 (as shown in FIG. 5) may be color coded a second color. The longitudinal slot 24 (as shown in FIG. 6A) may be color coded a third color. The first, second, and third colors may be of a typical color sequence such as red, white, and blue or red, yellow, and green to provide an obvious order in which the cutting guides are used.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for performing a shortening osteotomy on a bone comprising:

a main guide configured to be coupled to a bone and comprising a guide slot to guide at least one cut into the bone wherein the guide slot comprises first and second transverse portions and a longitudinal portion extending there between; and an interchangeable bone resection guide configured to engage and be disengaged from the main guide and to guide at least one cut into the bone, wherein the cuts formed using the main guide and the interchangeable bone resection guide cooperate to define two bone segments;

wherein the interchangeable bone resection guide is configured to overlie a portion of the main guide and comprises a pair of surfaces configured to align with the first and second transverse portions of the guide slot to define a pair of cutting guides.

2. The system according to claim 1, wherein the main guide comprises a plurality of holes and/or slots at least one of which is configured to guide a respective temporary fastener into the bone.

3. The system according to claim 2, wherein each temporary fastener comprises a pin.

4. The system according to claim 2, wherein the plurality of holes and/or slots extend obliquely through the main guide.

5. The system according to claim 2, wherein the plurality of holes and/or slots comprise slots that are configured to guide respective temporary fasteners into the bone so as to facilitate compression between the two bone segments.

6. The system according to claim 5, further comprising a clamp configured to engage the plurality of temporary fasteners positioned within the plurality of slots and to bias the plurality of temporary fasteners so as to compress the two bone segments together.

7. The system according to claim 1, wherein the interchangeable bone resection guide comprises at least one alignment hole.

8. The system according to claim 7, wherein the main guide comprises at least one alignment pin configured to engage the at least one alignment hole.

9. The system according to claim 1, further comprising at least a second interchangeable bone resection guide configured to engage and be disengaged from the main guide and to guide at least one cut into the bone having a different size and/or orientation than the at least one cut formed using the first interchangeable bone resection guide.

10. The system according to claim 1, wherein the main guide comprises first and second portions arranged in an L-shape.

11. The system according to claim 10, wherein the first portion of the main guide is configured to guide at least one cut into the bone, and wherein the second portion of the main guide comprises at least one hole configured to receive and guide a respective fastener into the bone so as to secure the two bone segments together.

12. A method of performing a shortening osteotomy on a bone comprising:
attaching a main guide to a bone;
coupling a bone resection guide to the main guide;
forming at least one cut using the bone resection guide;
forming at least one cut including a pair of transverse cuts and a longitudinal cut extending between the transverse cuts using the main guide such that the cuts formed using the main guide and the bone resection guide define two bone segments;
compressing the two bone segments together; and
securing the two bone segments together.

13. The method of claim 12, wherein attaching comprises attaching the main guide to the bone using a plurality of temporary fasteners guided into the bone with a plurality of respective holes defined in the main guide.

14. The method of claim 12, wherein coupling comprises mating at least one alignment hole defined in the bone resection guide into engagement with at least one respective alignment pin extending from the main guide.

15. The method of claim 12, wherein coupling comprises mating at least one alignment pin extending from the bone resection into engagement with at least one respective alignment hole defined in the main guide.

16. The method of claim 12, wherein compressing comprises urging together a plurality of temporary fasteners guided into the two bone segments.

17. The method of claim 16, wherein said urging comprises guiding the plurality of temporary fasteners along respective slots defined in the main guide.

18. The method of claim 12, wherein securing comprises securing the two bone segments together with at least one fastener extending through the two bone segments.

19. The method of claim 12, wherein forming the pair of transverse cuts comprises forming the transverse cuts perpendicular to a longitudinal axis of the bone.

20. The method of claim 12, wherein forming the longitudinal cut comprises forming the longitudinal cut parallel to a longitudinal axis of the bone.

21. The method of claim 12, further comprising detaching the first bone resection guide from the main guide, coupling a second bone resection guide to the main guide, and forming at least one cut using the second bone resection guide that has a different size than the at least one cut formed using the first bone resection guide.

22. The method of claim 12, wherein securing comprises securing the two bone segments together while the two bone segments are being compressed.

23. The method of claim 12, wherein attaching comprises orienting the main guide such that a first portion of the main guide contacts an exposed side of the bone while a second portion of the main guide contacts an anterior or a posterior side of the bone.

24. A system for performing a shortening osteotomy on a bone comprising:
a main guide configured to be coupled to a bone and comprising a guide slot to guide at least one cut into the bone wherein the guide slot comprises first and second transverse portions and a longitudinal portion extending there between;
an interchangeable bone resection guide configured to engage and be disengaged from the main guide and to guide at least one cut into the bone, wherein the cuts formed using the main guide and the interchangeable bone resection guide cooperate to define two bone segments; and
at least a second interchangeable bone resection guide configured to engage and be disengaged from the main guide and to guide at least one cut into the bone having a different size and/or orientation than the at least one cut formed using the first interchangeable bone resection guide.

25. The system according to claim 24, wherein the main guide comprises a plurality of holes and/or slots at least one of which is configured to guide a respective temporary fastener into the bone.

26. The system according to claim 25, wherein each temporary fastener comprises a pin.

27. The system according to claim 25, wherein the plurality of holes and/or slots extend obliquely through the main guide.

28. The system according to claim 25, wherein the plurality of holes and/or slots comprise slots that are configured to guide respective temporary fasteners into the bone so as to facilitate compression between the two bone segments.

29. The system according to claim 28, further comprising a clamp configured to engage the plurality of temporary fasteners positioned within the plurality of slots and to bias the plurality of temporary fasteners so as to compress the two bone segments together.

30. The device according to claim 24, wherein the interchangeable bone resection guide is configured to overlie a portion of the main guide and comprises a pair of surfaces configured to align with the first and second transverse portions of the guide slot to define a pair of cutting guides.

31. The system according to claim 24, wherein the interchangeable bone resection guide comprises at least one alignment hole.

32. The system according to claim 31, wherein the main guide comprises at least one alignment pin configured to engage the at least one alignment hole.

33. The system according to claim 24, wherein the main guide comprises first and second portions arranged in an L-shape.

34. The system according to claim 33, wherein the first portion of the main guide is configured to guide at least one cut into the bone, and wherein the second portion of the main guide comprises at least one hole configured to receive and guide a respective fastener into the bone so as to secure the two bone segments together.

* * * * *